United States Patent [19]

Makino et al.

[11] Patent Number: 5,912,011
[45] Date of Patent: Jun. 15, 1999

[54] SOLVENT SYSTEM TO BE ENCLOSED IN CAPSULES

[75] Inventors: Hirokazu Makino; Ichiro Hakamada, both of Kakegawa; Osamu Yamada, Yokaham, all of Japan

[73] Assignee: R. P. Scherer Corporation, Troy, Mich.

[21] Appl. No.: 08/400,487

[22] Filed: Mar. 8, 1995

Related U.S. Application Data

[62] Division of application No. 08/104,150, filed as application No. PCT/US92/10773, Dec. 18, 1992, abandoned.

[30] Foreign Application Priority Data

Dec. 19, 1991 [JP] Japan .................................. 3-337138

[51] Int. Cl.⁶ .................. A61K 9/08; A61K 9/48
[52] U.S. Cl. .................. 424/455; 424/452; 514/962
[58] Field of Search .................. 424/400, 455, 424/451, 452; 514/962

[56] References Cited

U.S. PATENT DOCUMENTS

| | | | |
|---|---|---|---|
| 3,202,578 | 8/1965 | Parker | 424/78.01 |
| 4,665,098 | 5/1987 | Gibbs et al. | 514/613 |
| 4,690,823 | 9/1987 | Lohner et al. | 424/455 |
| 4,780,316 | 10/1988 | Brox | 424/455 |
| 4,795,643 | 1/1989 | Seth | 424/455 |
| 4,888,239 | 12/1989 | Brox | |
| 4,927,638 | 5/1990 | Bykadi et al. | 424/455 |
| 5,071,643 | 12/1991 | Yu et al. | 424/455 |
| 5,175,002 | 12/1992 | Toroslan | 424/456 |
| 5,178,877 | 1/1993 | Garren et al. | 424/455 |
| 5,200,192 | 4/1993 | Wimmer | 424/455 |
| 5,206,219 | 4/1993 | Desai | 424/455 |
| 5,360,615 | 11/1994 | Yu et al. | 424/455 |
| 5,376,688 | 12/1994 | Morton et al. | 514/786 |
| 5,559,121 | 9/1996 | Harrison et al. | 514/291 |
| 5,665,384 | 9/1997 | Courteille et al. | 424/451 |
| 5,670,159 | 9/1997 | Morton et al. | 424/401 |

OTHER PUBLICATIONS

Patel et al., 1992, Drug Development and Industrial Pharmacy 18(1): 1–19 "Factors Affecting the Chemical Stability of Carboxylic Acid Drugs in Enhanced Solubility System (ESS) Softgel Formulations Based on Polyethylene Glycol (PEG)."

*Primary Examiner*—Robert H. Harrison
*Attorney, Agent, or Firm*—McDonnell Boehnen Hulbert & Berghoff

[57] ABSTRACT

To increase the solubility of acidic medicines a high concentration solvent system to be encapsulated comprises a) 10–80% by weight acidic medicine, b) 0.1–1.0 mole hydroxide ions for one mole equivalent of said medicine, and c) 1–20% by weight water.

included in polyoxyethylene sorbitan fatty acid ester as the solvent.

10 Claims, No Drawings

SOLVENT SYSTEM TO BE ENCLOSED IN CAPSULES

This application is a division of application Ser. No. 08/104,150, filed on Aug. 11, 1993, now abandoned, which is a 371 of PCT/US92/10773 filed Dec. 18, 1992.

BACKGROUND OF THE INVENTION

In general, it is preferable that medicines are easy to swallow and in the administrational form of small volume or quantity. In addition, it is desirable that their ingredients are uniformly distributed and they are administered efficiently, e.g., in a high concentration. Encapsulation can satisfy such purposes as discussed in a Japanese patent application titled "Simplified Encapsulation of Medicines," which has been published in the Japanese Unexamined Patent Gazette No. 1-502185.

This Gazette discloses a specific solvent solution system that is to be encapsulated and composed of an ionizable medicine, hydroxide ions or hydrogen ions enough to enhance the solubility of said medicine, and a specified amount of water and polyethylene glycol (PEG).

However, this solvent system using PEG can cause a local reaction due to existing hydroxide ions depending on the properties of other components in the capsule. As the result, an ester may be produced and, thereby, may cause the purity of the encapsulated contents to be lowered.

The inventors of the present invention have earnestly investigated the purity deterioration of the solute component (medicine) due to its reaction with the solvent and found that polyoxyethylene sorbitan fatty acid ester (hereafter, abbreviated POSE) is a solvent useful for preventing the deterioration of purity, and have reached the present invention.

1. Field of the Invention

The present invention relates to a solvent system that includes a highly concentrated acidic medicine, the solubility of which is enhanced by partial ionization of said medicine.

This solvent system is used by being enclosed in soft gels (soft elastic gelatin capsules) or hard gelatin shells.

2. Outline of the Invention

The present invention relates to a high concentration solvent system to be enclosed in capsules, said system being composed of a) 10–80% by weight acidic medicine, b) 0.1–1.0 mole hydroxide ions for one mole of said medicine, and c) 1–20% by weight water included in POSE, the mean molecular weight of said POSE being 600–3000.

SUMMARY OF THE INVENTION

Hereafter, the present invention will be explained in detail.

a) Ibuprofen, Naproxen, Indomethacin, Acetaminophen, etc. may be exemplified as among the acidic medicines to be used in this invention.

Said acidic medicine is selectively used in the range of about 10–80% by weight for the amount of POSE in consideration of the kind of acidic medicine used. The use of the medicine in the region under or over said range is less advantageous because the system may become too low in concentration in the former while it may become inhomogeneous, causing the crystallization of the acidic medicine in the form of insoluble substances in the latter.

b) In the present invention, about 0.1–1.0 mole hydroxide ions is used for each molar equivalent of said acidic medicine.

Hydroxide ions originated, for example, from sodium and/or potassium hydroxide, are used together with water. Use of hydroxide ions in the concentration under or over the above-mentioned range is less advantageous because the acidic medicine may not be dissolved in the former, causing an inhomogeneous phase system and, on the other hand, the gelatin constituting the shell of capsules tends to be hydrolyzed in the latter, causing leaking capsules c) in the present invention, about 1–20% by weight water is included in POSE. If the water content is lower than about 1% by weight, the ionization of the acidic medicine might be incomplete though it depends on the nature of the medicine used, making the desired solubility unattainable. On the other hand, if the water content is more than about 20% by weight, the capsule containing such water may be softened and impractical.

In the present invention, this water can be added directly to the POSE or the acidic medicine; otherwise it can be added to the hydroxide to be used in order to obtain an aqueous solution of alkaline hydroxide, which is afterwards added to the POSE.

In the present invention, POSEs with mean molecular weights of approximately 600–3000 are preferably used. Such POSEs are well known, for example, under the trade name of Tween (Atlas Powder Co.) and are easily available in the market. Specific POSEs useful in the present invention include:

TWEEN 20 ethylene oxide condensate of sorbitanmonolaurate

TWEEN 21 ethylene oxide condensate of sorbitanmonolaurate

TWEEN 40 ethylene oxide condensate of sorbitanmonopalmitate

TWEEN 60 ethylene oxide condensate of sorbitan-monostearate

TWEEN 61 ethylene oxide condensate of sorbitan-monostearate

TWEEN 65 ethylene oxide condensate of sorbitantristearate

TWEEN 80 ethylene oxide condensate of sorbitanmonooleate

TWEEN 81 ethylene oxide condensate of sorbitanmonooleate

TWEEN 85 ethylene oxide condensate of sorbitantrioleate

Effects of the Invention

The effects of the present invention may be listed as follows:

a) The solubility of acidic medicine can be increased by about 4–400%.

b) The chemical stability of the included medicine is higher than that in the case where PEG is used as the primary solvent.

c) When filled in capsules, the capsule contents can be reduced in volume.

d) No deteriorative effects are inflicted on the shell of capsules.

DESCRIPTION OF THE PREFERRED EMBODIMENTS

Some embodiments will be described with emphasis laid on the contrast with PEG so as to explain the present invention in further detail.

EXAMPLE 1

10 g each of Ibuprofen and Naproxen, both acidic medicines, was partially neutralized with a potassium hydroxide solution in PEG 400 and polyoxyethylene sorbitan fatty acid easter ("polysorbate" in Japanese Pharmacopcia; trade name: TWEEN) and the solubilities of these medicines were measured.

It is possible as shown in Table 1 to increase the solubility of the medicine.

TABLE 1

| Medicine | Unit Dose (mg) | PEG 400 (Control) | | TWEEN 80 (This Invention) | |
|---|---|---|---|---|---|
| | | Solubility (%) | Capsule Size | Solubility (%) | Capsule Size |
| Ibuprofen | 150 | 25 | 11 | 75 | 4 |
| Naproxen | 100 | 15 | 18 | 55 | 4 |

EXAMPLE 2

Ibuprofen in various polyoxyethylene sorbitan fatty acid ester solutions (TWEEN) was partially neutralized with an alkaline solution and preserved at 105° C. for 44 hours. The amount of ester produced between the acidic medicine and the solvent and the content of the remaining Ibuprofen were measured and compared with those in the case where PEG is used instead of POSE.

It is shown in Table 2 that the formation rate of ester can be made lower than that in the case where PEG is used as solvent.

EXAMPLE 3

Naproxen in various polyoxyethylene sorbitan fatty acid ester solutions was partially neutralized with an alkaline solution and preserved at 105° C. for 44 hours. The amount of ester produced between the acidic medicine and the solvent and the content of the remaining Naproxen were measured to be compared with those in the case where PEG is used.

It is shown in Table 3 that the formation rate of ester can be made lower than that in the case where PEG is used as solvent.

TABLE 2

| | Control Sample | | | | This Invention | | | |
|---|---|---|---|---|---|---|---|---|
| | A | B | C | D | E | F | G | H |
| Ibuprofen | 200 | 200 | 200 | 200 | 200 | 200 | 200 | 200 |
| PEG 400 | 250 | 125 | 125 | 0 | 0 | 0 | 0 | 0 |
| PEG 1500 | 0 | 125 | 0 | 125 | 0 | 0 | 0 | 0 |
| TWEEN 20 | 0 | 0 | 0 | 0 | 250 | 0 | 0 | 0 |
| TWEEN 40 | 0 | 0 | 0 | 0 | 0 | 250 | 0 | 0 |
| TWEEN 60 | 0 | 0 | 0 | 0 | 0 | 0 | 250 | 0 |
| TWEEN 80 | 0 | 0 | 0 | 0 | 0 | 0 | 0 | 250 |
| Propylene Glycol | 0 | 0 | 125 | 125 | 0 | 0 | 0 | 0 |
| NaOH | 12 | 12 | 12 | 12 | 12 | 12 | 12 | 12 |
| Pufified Water | 51 | 51 | 51 | 51 | 51 | 51 | 51 | 51 |
| Total Content (mg) | 513 | 513 | 513 | 513 | 513 | 513 | 513 | 513 |
| Alkali n/e | 0.29 after treated | 0.29 after treated | 0.29 after treated | 0.29 after treated | 0.29 after treated | 0.29 after treated | 0.29 after treated | 0.29 after treated |
| PEG Ester (%) | 8.5 | 7.5 | 2.8 | 1.4 | ND | ND | ND | ND |
| PG Ester (%) | ND | ND | 13.1 | 11.2 | ND | ND | ND | ND |
| Ibuprofen (%) | 90.5 | 90.3 | 83.0 | 85.7 | 93.8 | 94.0 | 94.1 | 94.8 |

After Treated . . . Value determined after preserved at 105° C. for 44 hours
ND: Not Detected

TABLE 3

|  | Control Samples | | | | This Invention | | | |
| --- | --- | --- | --- | --- | --- | --- | --- | --- |
|  | I | J | K | L | M | N | O | P |
| Naproxen | 100 | 100 | 100 | 100 | 100 | 100 | 100 | 100 |
| PEG 600 | 168 | 0 | 0 | 0 | 0 | 0 | 0 | 0 |
| PEG 400 | 0 | 168 | 166 | 168 | 0 | 0 | 0 | 0 |
| TWEEN 20 | 0 | 0 | 0 | 0 | 209 | 0 | 0 | 0 |
| TWEEN 40 | 0 | 0 | 0 | 0 | 0 | 209 | 0 | 0 |
| TWEEN 60 | 0 | 0 | 0 | 0 | 0 | 0 | 209 | 0 |
| TWEEN 80 | 0 | 0 | 0 | 0 | 0 | 0 | 0 | 209 |
| KOH | 11 | 12 | 0 | 12 | 12 | 12 | 12 | 12 |
| NaOH | 0 | 0 | 8 | 0 | 0 | 0 | 0 | 0 |
| Purified Water | 11 | 12 | 17 | 12 | 12 | 12 | 12 | 12 |
| Total Content (mg) | 290 | 292 | 291 | 292 | 333 | 333 | 333 | 333 |
| Alkali n/e | 0.47 after treated | 0.49 after treated | 0.47 after treated | 0.49 after treated | 0.49 after treated | 0.49 after treated | 0.49 after treated | 0.49 after treated |
| PEG Ester (%) | 4.6 | 7.4 | 6.1 | 5.1 | ND | ND | ND | ND |
| Naproxen (%) | 95.4 | 92.6 | 93.9 | 93.9 | 97.4 | 98.1 | 98.3 | 98.5 |

After Treated . . . Value determined after preserved at 105° C. for 44 hours
ND: Not Detected

EXAMPLE 4

Ibuprofen dissolved separate in three kinds of solvents—two kinds of polyoxyethylene sorbitan fatty acid ester (TWEEN 20 and TWEEN 80) and polyethylene glycol—was partially neutralized (0.3–0.4 m/e) with alkaline solutions and the obtained solutions were encapsulated into soft capsules whose shell films are made of 100 parts gelatin, 35 parts glycerin and 15 parts sorbitol using a rotary soft-capsule filling machine, producing each capsule whose fill weight is approximately 390 mg.

It was found in these capsules preserved at 40° C. for 6 months that the formation rate of ester is lower in the capsules filled with POSE than in those filled with PEG.

TABLE 4

|  | No 1 | No 2 | No 3 | No 4 | No 5 | No 6 | No 7 | No 8 | No 9 |
| --- | --- | --- | --- | --- | --- | --- | --- | --- | --- |
| Formulation | | | | | | | | | |
| Ibuprofen | 155 | 155 | 155 | 155 | 155 | 155 | 155 | 155 | 155 |
| PEG 400 | 95 | 95 | 95 | 95 | 171 | 95 | 95 | 0 | 0 |
| PEG 1500 | 95 | 95 | 95 | 95 | 19 | 0 | 0 | 0 | 0 |
| TWEEN 20 | 0 | 0 | 0 | 0 | 0 | 95 | 0 | 190 | 0 |
| TWEEN 80 | 0 | 0 | 0 | 0 | 0 | 0 | 95 | 0 | 190 |
| NaOH | 9 | 0 | 9 | 0 | 9 | 9 | 9 | 0 | 0 |
| KOH | 0 | 13 | 0 | 13 | 0 | 0 | 0 | 13 | 13 |
| Fill Quantity (ag) | 385 | 389 | 385 | 389 | 385 | 385 | 385 | 389 | 389 |
| Stability Test Results (%) | | | | | | | | | |
| 1 month 50° C. | 91.0 | 94.1 | 97.4 | 96.8 | 95.5 | 96.1 | 97.3 | 99.8 | 101.3 |
| 3 mths Room Temp. | 96.7 | 94.8 | 98.1 | 97.4 | 98.1 | 99.3 | 98.7 | 99.5 | 99.4 |
| 3 months 40° C. | 94.8 | 94.8 | 94.8 | 94.8 | 94.2 | 96.7 | 96.8 | 98.2 | 98.1 |
| 6 mths Room Temp. | 96.7 | 96.1 | 95.5 | 94.8 | 95.5 | 99.3 | 96.1 | 99.9 | 100.6 |
| 6 months 40° C. | 92.8 | 93.5 | 92.9 | 91.6 | 89.7 | 92.8 | 95.5 | 97.2 | 97.4 |
| Change in Ester Formation with Time (%) | | | | | | | | | |
| Amount of ester after preserved at 40° C. for 3 mths | | | | | | | | | |
| Glycerin Ester | 2.1 | 2.3 | 2.1 | 2.1 | 2.1 | 2.4 | 1.8 | 1.8 | 1.7 |
| PBG Ester | 1.7 | 1.7 | 1.8 | 1.6 | 1.8 | 1.1 | 1.1 | 0.0 | 0.0 |

TABLE 4-continued

|  | No 1 | No 2 | No 3 | No 4 | No 5 | No 6 | No 7 | No 8 | No 9 |
|---|---|---|---|---|---|---|---|---|---|
| Amount of ester after preserved at 40° C. for 6 months | | | | | | | | | |
| Glycerin Ester | 2.1 | 2.5 | 2.1 | 2.1 | 2.1 | 2.5 | 1.8 | 1.8 | 1.8 |
| PBG Ester | 1.1 | 1.6 | 1.9 | 1.8 | 1.8 | 1.5 | 1.5 | 0.0 | 0.0 |

EXAMPLE 5

Naproxen separately dissolved in three kinds of solvents—two kinds of POSE (TWEEN 20, TWEEN 80) and PEG—was partially neutralized with alkaline solutions and the obtained solutions were encapsulated into soft capsules whose shell films are made of 100 parts gelatin, 30 parts glycerin and 15 parts sorbitol using a rotary soft-capsule filling machine, producing each capsule whose fill weight is approximately 574 mg.

It was found in these capsules preserved for 4 months at 40° C. that the formation rate of ester is lower in the capsules filled with POSE than those in PEG.

TABLE 5

|  |  | No 1 | No 2 | No 3 | No 4 |
|---|---|---|---|---|---|
| Formulation | | | | | |
| Naproxen | | 200 | 200 | 200 | 200 |
| PEG 400 | | 330 | 165 | 0 | 0 |
| PEG 1500 | | 0 | 165 | 0 | 0 |
| TWEEN 20 | | 0 | 0 | 330 | 0 |
| TWEEN 80 | | 0 | 0 | 0 | 330 |
| KOH | | 22 | 22 | 22 | 13 |
| Purified Water | | 22 | 22 | 22 | 31 |
| Fill Quantity (mg) | | 574 | 574 | 574 | 574 |
| Results of Stability Test (%) | | | | | |
| 1 mth | 50° C. | 98.3 | 98.5 | 99.1 | 99.3 |
| 3 mths | Room Temp. | 99.6 | 99.5 | 99.9 | 99.9 |
| 3 mths | 40° C. | 98.9 | 99.1 | 99.6 | 99.7 |
| 6 mths | Room Temp. | 99.8 | 99.3 | 99.7 | 99.7 |
| 6 mths | 40° C. | 97.3 | 97.6 | 98.9 | 99.2 |

We claim as our invention:

1. An aqueous pharmaceutical solution suitable for encapsulation in gelatin capsules, said solution consisting essentially of from about 48% to about 63% by weight, based on the weight of the solution, of a polyoxyethylene sorbitan fatty acid ester solvent having a mean molecular weight between 600 and 3000 and 1–20% by weight, based on the weight of the polyoxyethylene sorbitan fatty acid ester solvent, of water, with dissolved therein a combination of an acidic medicine and a source of hydroxide ions sufficient to provide 0.1–1.0 mole of hydroxide ions for each mole of said acidic medicine.

2. A solution as claimed in claim 1, wherein said medicine is ibuprofen or naproxen.

3. A solution as claimed in claim 1, wherein said source of hydroxide ions is an alkaline hydroxide.

4. A pharmaceutical composition comprising gelatin capsules having encapsulated therein an aqueous solution as claimed in claim 3.

5. An aqueous pharmaceutical solution suitable for encapsulation in gelatin capsules, said solution consisting essentially of from about 48% to about 63% by weight based on the weight of the solution of a polyoxyethylene sorbitan fatty acid ester solvent having a mean molecular weight of between 600 and 3000 and 1–20% by weight, based on the weight of the polyoxyethylene sorbitan fatty acid ester solvent, of water, with dissolved therein a combination of 10%–80% by weight, based on the weight of the polyoxyethylene sorbitan fatty acid ester solvent, of an acidic medicine and a source of hydroxide ions sufficient to provide 0.1–1.0 mole of hydroxide ions for each mole of said acidic medicine.

6. A medicinal composition of an acidic medicine suitable for encapsulation in gelatin capsules for subsequent oral administration consisting essentially of:

(a) an acidic medicine agent;

(b) about 1–20% by weight of water based on the weight of polyoxyethylene sorbitan fatty acid ester;

(c) about 0.1–1.0 mole of hydroxide ions for each mole of said medicine; and (d) from about 48% to about 63% by weight, based on the weight of the composition of polyoxyethylene sorbitan fatty acid ester, wherein the mean molecular weight of said polyoxyethylene sorbitan fatty acid ester is between about 600 and 3000.

7. A medicinal composition described in claim 6, wherein said acidic medicine agent is ibuprofen or naproxen.

8. A medicinal composition described in claim 6, wherein said hydroxide ions originate from an alkaline hydroxide.

9. A medicinal composition according to claim 6 enclosed in a soft gelatin capsule.

10. A medicinal composition comprising a gelatin shell and a fill material consisting essentially of a solution of:

(a) an acidic medicine agent;

(b) about 1–20% by weight of water based on the weight of polyoxyethylene sorbitan fatty acid ester;

(c) about 0.1–1.0 mole of hydroxide ions for each mole of said medicine; and (d) from about 48% to about 63% by weight, based on the weight of the composition, of polyoxyethylene sorbitan fatty acid ester, wherein the mean molecular weight of said polyoxyethylene sorbitan fatty acid ester is between about 600 and 3000.

* * * * *